United States Patent [19]
Reichenberger

[11] Patent Number: 5,817,021
[45] Date of Patent: Oct. 6, 1998

[54] THERAPY APPARATUS FOR TREATING CONDITIONS OF THE HEART AND HEART-PROXIMATE VESSELS

[75] Inventor: Helmut Reichenberger, Eckental, Germany

[73] Assignee: Siemens Aktiengesellschaft, Munich, Germany

[21] Appl. No.: 525,747

[22] PCT Filed: Mar. 22, 1994

[86] PCT No.: PCT/DE94/00327

§ 371 Date: Oct. 3, 1995

§ 102(e) Date: Oct. 3, 1995

[87] PCT Pub. No.: WO94/23793

PCT Pub. Date: Oct. 27, 1994

[30] Foreign Application Priority Data

Apr. 15, 1993 [DE] Germany .......................... 43 12 264.7

[51] Int. Cl.⁶ .................................................. H61B 17/22
[52] U.S. Cl. ................................................. 600/439; 601/3
[58] Field of Search .......................... 128/660.03; 601/3, 601/2, 4; 607/96; 600/439

[56] References Cited

U.S. PATENT DOCUMENTS

| | | | |
|---|---|---|---|
| 4,858,613 | 8/1989 | Fry et al. | 128/660.03 |
| 4,957,099 | 9/1990 | Hassler | 601/4 |
| 4,960,109 | 10/1990 | Lele | 601/3 |
| 5,036,855 | 8/1991 | Fry et al. | |
| 5,193,527 | 3/1993 | Schafer | 601/2 |
| 5,472,405 | 12/1995 | Buchholtz et al. | 128/660.03 |
| 5,474,071 | 12/1995 | Chapelon et al. | 601/3 |
| 5,526,815 | 6/1996 | Granz et al. | 601/3 |

FOREIGN PATENT DOCUMENTS

| | | |
|---|---|---|
| 0 404 121 | 12/1990 | European Pat. Off. . |
| OS 30 38 445 | 5/1982 | Germany . |
| OS 31 50 513 | 6/1983 | Germany . |
| OS 39 00 433 | 7/1990 | Germany . |
| OS 39 32 967 | 4/1991 | Germany . |
| OS 40 05 743 | 8/1991 | Germany . |
| OS 42 07 463 | 9/1993 | Germany . |

OTHER PUBLICATIONS

Transösophageale Echo Computer Tomographie ("Echo–CT") Wollschläger et al., Biomedizinische Technik, vol. 34, Supplementary vol., p. 10 (1989).

Primary Examiner—Brian Casler
Attorney, Agent, or Firm—Hill & Simpson

[57] ABSTRACT

In a therapy apparatus and method for treating conditions of the heart and, particularly, of heart-proximate vessels with therapeutic ultrasound waves having a therapeutically effective region. The therapy apparatus generates therapeutic ultrasound waves with such an intensity that tissue modifications, particularly necrotization, are produced in the tissue located in the region of influence. The therapy apparatus preferably contains an ultrasound source that can be transesophageally applied.

31 Claims, 4 Drawing Sheets

THERAPY APPARATUS FOR TREATING CONDITIONS OF THE HEART AND HEART-PROXIMATE VESSELS

BACKGROUND OF THE INVENTION

1. Field of the Invention

The invention is directed to a therapy apparatus for treating conditions of the heart and, in particular, heart-proximate vessels with therapeutic acoustic waves having a region of influence, the therapy apparatus being of the type having a therapeutic ultrasound source.

2. Description of the Prior Art

German OS 30 38 445 discloses an apparatus of the above type. This apparatus contains a shock wave source integrated in a catheter introducible into the esophagus. The focussed shock waves generated by the shockwave source are introduced into the heart in order to stimulate it.

German OS 39 00 433 discloses another apparatus of the above type. This apparatus contains one or more ultrasound sources that can be extracorporeally applied. The therapeutic ultrasound waves generated by the ultrasound source or sources serve for treating scleroses, for example in the region of the coronary vessels. A re-emulsification of the lipids deposited at the vessel wall in the sclerotic regions is to be effected by the therapeutic ultrasound waves.

It is in fact possible to influence symptoms with this known therapy apparatus, for example in the case of disorders of the heart rhythm or scleroses. As a rule, however, there is no possibility of achieving a longterm influence in focal pathogenic areas such as, for example, accessoral bundles in the case of the WPW symptom or trigger zones for arrhythmias.

German OS 31 50 513 discloses a therapy apparatus for treatment with therapeutic ultrasound waves having a region of influence, the apparatus having an ultrasound source which generates the therapeutic ultrasound waves with an intensity such that tissue modifications due to the thermal effect of the ultrasound waves are produced in the tissue disposed in the region of influence. The apparatus contains a number of therapeutic ultrasound transducers which can be oriented such that the ultrasound waves respectively emitted by the individual transducers are superimposed in the region to be treated. The source of therapeutic ultrasound waves in this known therapy apparatus is only suitable for extracorporeal application.

SUMMARY OF THE INVENTION

An object of the invention to provide a therapy apparatus of the type initially described such that a long term influencing of pathogenic areas, particularly pathogenic foci, is possible.

The above object is achieved in accordance with the principles of the present invention in a therapy apparatus and method for treating conditions of the heart and, in particular, heart-proximate vessels, with therapeutic acoustic waves having a region of influence, i.e., a therapeutically effective region, wherein ultrasound waves are generated with such an intensity that tissue modifications are produced by the thermal effect of the ultrasound waves in the tissue located in the region of influence. The apparatus is dimensioned so that it can be transesophageally applied, and the source of therapeutic waves includes a number of therapeutic ultrasound transducers which can be oriented relative to each other so that the ultrasound waves respectively emitted by the sources are superimposed in the region to be treated.

There is thus the possibility of suppressing focal pathogenic regions by charging with therapeutic ultrasound waves. It is especially advantageous in this context when the intensity of the therapeutic ultrasound waves produces necrotization of the heart tissue located in the region of influence since a reliable suppression of the focal pathogenic regions is then assured. Since the ultrasound source is dimensioned such that it can be transesophageally applied (through the esophagus), the heart located inside the ribs is accessible for the therapeutic ultrasound waves without further ado, differing from the case of extracorporeally generated therapeutic ultrasound waves. For the sake of a short treatment duration, the ultrasound source comprises a plurality of therapeutic ultrasound transducers that can be aligned such that the ultrasound waves emanating from them superimpose in the region to be respectively treated because the maximum dimensions that a transducer element of a transesophageally applied ultrasound source can comprise for anatomical reasons, namely, do not allow the ultrasound energy required for achieving the success of the treatment to be applied to the region respectively to be treated in an adequately short time under all circumstances when a single ultrasound transducer is employed.

It should be noted that European Application 0 404 121 and U.S. Pat. No. 5,036,855 disclose therapy apparatuses that allow tumor tissue to be treated by thermal effect of ultrasound. Unlike the apparatus disclosed in German OS 39 00 433, however, these two latter two references teach that permanent tissue modifications are precisely what are to be avoided when treating vessels and the heart by pulsed emission of the ultrasound.

As a result of the anatomically favorable position of the esophagus and the heart relative to one another, it is expedient when the ultrasound source contains a diagnostic ultrasound transducer that is a component of an ultrasound locating means for locating the region to be treated, since an especially good image quality of the ultrasound images produced with the ultrasound locating means is then assured.

In order to be able to easily introduce the therapeutic ultrasound source into the esophagus, in an embodiment of the invention the therapeutic ultrasound transducer/transducers, and possibly the diagnostic ultrasound transducer, are components of an arrestable, chain-like structure, whereby the structure is flexible in the non-arrested condition and is substantially rigid in the arrested condition. The ultrasound source can be easily applied as a result of the flexibility established in the non-arrested condition, whereas a defined allocation of the elements of the ultrasound source and the heart or the vessels to be treated relative to one another is established for treatment as a result of the rigidity present in the arrested condition. A diagnostic ultrasound applicator constructed chain-like that can be transesophageally applied for sonography of the heart is described, moreover, in "Transösophageale Echo Computer Tomographie", Willschläger et al., *Biomedizinische Technik*, Volume 34, Supplementary Volume, page 10, 1989.

Since the individual regions of the heart or the blood vessels are displaced relative to the ultrasound source accepted in the esophagus as a consequence of the heart activity, means for detecting the heart activity are provided according to a preferred version of the invention. The means for detecting heart activity enable emission of therapeutic ultrasound waves only during such phases of the heart activity wherein the heart and the vessels are at relative mechanical rest. It is then assured that only those regions of the heart or of the vessels that truly need treatment are subject to a treatment.

In another embodiment of the invention, at least one extracorporeally applied therapeutic ultrasound source is employed in addition to the transesophageally applied source, particularly an intercostally or subcostally applied therapeutic ultrasound source, i.e. a source applied between the ribs or under the costal arch therefor. This extracorporeally applied source is preferably alignable such that the therapeutic ultrasound waves emanating therefrom are superimposed at least in the region of influence with those emanating from the ultrasound source. As a result, the intensity of the ultrasound waves in the region of influence can be increased for achieving a short treatment duration. The therapeutic ultrasound waves emanating from at least one of the ultrasound sources, or the therapeutic ultrasound waves emanating from at least one of the therapeutic ultrasound transducers, are focussed onto a focus zone. It is then possible to displace the zone of influence into the region to be treated by displacing the focus zone inside that region wherein the therapeutic ultrasound waves are superimposed. It is especially advantageous in this context when a larger and a smaller focus zone are provided and the displacement of the zone of influence ensues by displacement of the smaller focus zone within the larger.

In another version of the invention, at least one of the ultrasound sources or at least one of the therapeutic ultrasound transducers emits the therapeutic ultrasound waves pulse-like. This results in the intensity of the therapeutic ultrasound waves required for achieving a therapeutic effect being present only during the pulse-like emission.

In a further version of the invention the ultrasound waves have an energy density in the zone of influence, and the pulse duration given a pulse-like emission of the therapeutic ultrasound waves is selected, such that the acoustic energy supplied to the zone of influence during a heart action produces the desired therapeutic effect.

In order to enable a localization of the focal pathogenic region to be respectively treated, it is expedient to provide means for determining the spatial position of the pathological region to be treated, such means preferably containing a means for producing magnetocardiograms with which magnetic field sources can be spatially localized, or a means for EKG mapping. There is then the possibility, given the occurrence of symptoms, to localize the focus from which these symptoms proceed and to then subsequently treat the focus.

In order to enable an effective monitoring of the therapy process, it is expedient to provide means for determining the temperature in the region of influence, such means preferably containing a means for the at least qualitative determination of the temperature from successive ultrasound images.

DESCRIPTION OF THE PREFERRED EMBODIMENTS

Figure 1:
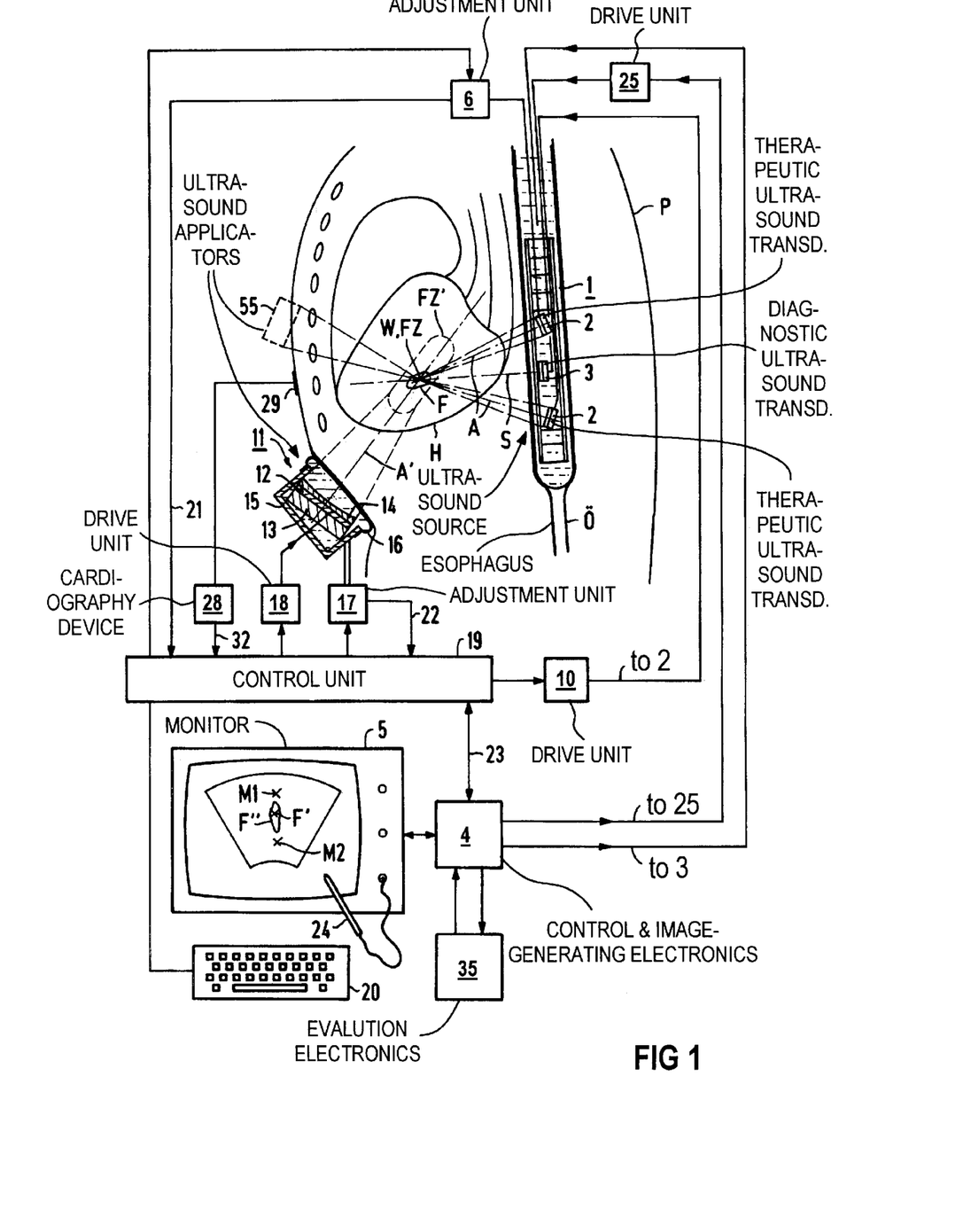
FIG. 1 is a schematic block diagram of a therapy apparatus constructed in accordance with the principles of the present invention, applied to a human body shown in sagittal section.

The therapy apparatus shown in FIG. 1 has an ultrasound source 1 that can be applied through the esophagus (referenced Ö) of the patient P, the ultrasound source 1 being filled with a fluid acoustic propagation medium, for example water, and containing two therapeutic ultrasound transducers 2. The ultrasound source 1 is positioned in the esophagus such that the therapeutic ultrasound transducers 2 are located in close proximity to the heart H to be treated.

The ultrasound source 1 also contains a diagnostic ultrasound transducer 3 that is a component of an ultrasound locating system and serves the purpose of localizing the region to be treated, for example a pathological focus F that is the starting point of disorders in heart rhythm. The diagnostic ultrasound transducer 3 is pivotable around an axis lying in the plane of the drawings with a drive unit 25 such that, in collaboration with a control and image-generating electronics 4, it is in the position to produce ultrasound B-images of a plane E residing at a right angle relative to the plane of the drawing (see FIG. 2) and to display these images on a monitor 5. The intersecting line S of the scanned plane with the plane of the drawing is entered in FIG. 1.

In the implementation of a treatment, the therapeutic ultrasound transducers 2 emit therapeutic ultrasound waves. The therapeutic ultrasound transducers 2 are accepted in the ultrasound source 1 so as to be pivotable around axes residing at a right angle relative to the plane of the drawing so that, by consulting the ultrasound image displayed on the monitor 5 by the therapeutic ultrasound transducer 3 and the control and image-generating unit 4, they can be aligned with the assistance of an adjustment means 6 for the implementation of a treatment. In this alignment, the therapeutic ultrasound waves emanating from the two therapeutic ultrasound transducers 2 are superimposed in the focus F to be treated that is placed in the plane E, the edge rays of the therapeutic ultrasound waves being indicated with broken lines.

Figures 2, 4:
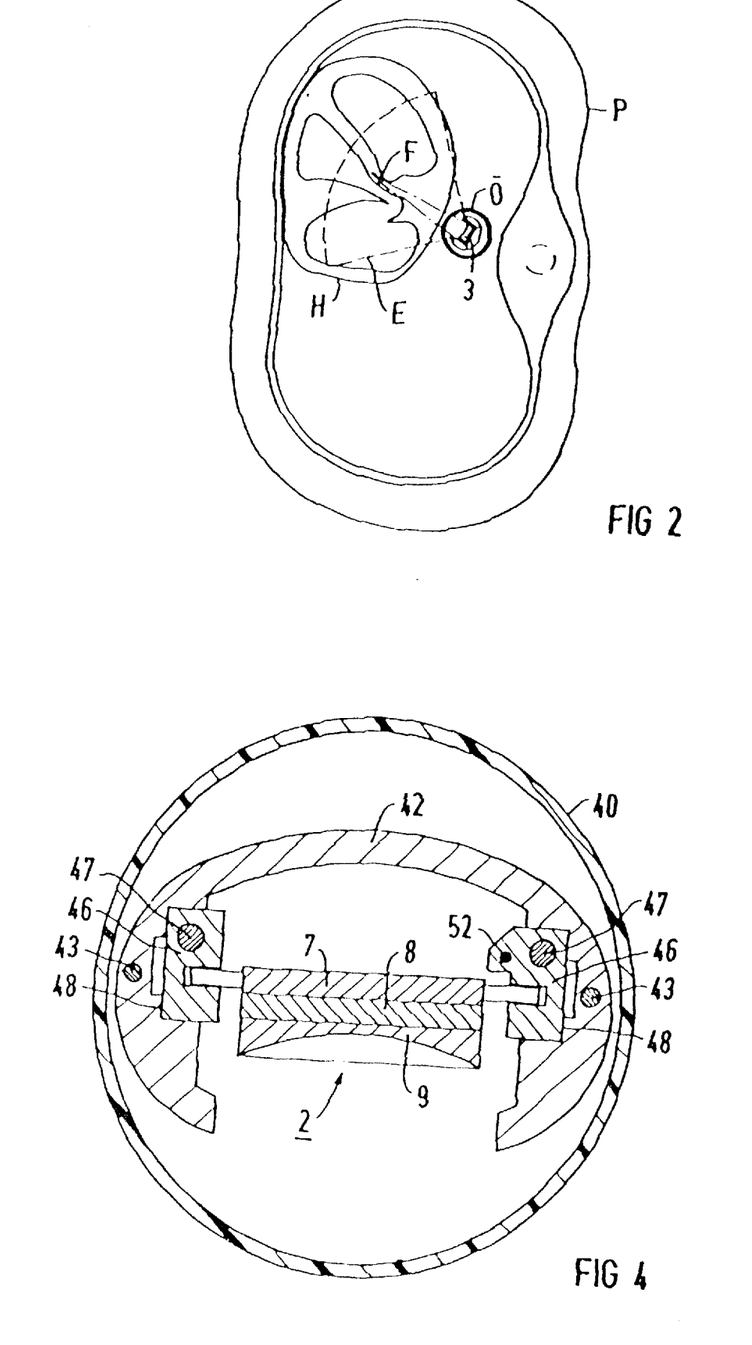
FIG. 2 illustrates the apparatus of FIG. 1 applied to the body shown in a transversal section.
FIGS. 4, 5 and 6 respectively show sections taken along line IV—IV, line V—V, and line VI—VI of FIG. 3.

The therapeutic ultrasound transducers 2 are piezoelectric transducers that, according to FIG. 4, each contain a piezoelectric transducer element 8 with a preceding acoustic positive lens 9 applied on a backing (carrier) 7. The acoustic waves generated by the transducer elements are focussed onto a focus zone FZ by the acoustic positive lenses 9.

In the implementation of a treatment, the therapeutic ultrasound transducers 2 are aligned such that their respective focus zones FZ overlap in the focus F to be treated. In a known way, the transducer elements 8 can be subdivided into a plurality of annular zones that can be driven with chronological delay for emitting therapeutic ultrasound waves, so that it is possible to displace the position of each focus zone FZ along each acoustic axis A electronically. The positive lenses 9 can then be omitted under certain circumstances.

A drive unit 10 that makes the currents required for the operation of the therapeutic ultrasound transducers 2 available is allocated to the therapeutic ultrasound transducers 2. If the therapeutic ultrasound transducers 2 have an electronically displaceable focus zone FZ, the electronic devices required therefor are integrated into the drive unit 10.

A therapeutic ultrasound applicator 11 that can be extracorporeally applied, namely subcostally, i.e. under the costal arch, is provided in addition to the ultrasound source 1. The ultrasound applicator 11 also contains a piezoelectric transducer element 12 that is attached on a backing 13 and is provided with an acoustic positive lens. In a way not shown in detail, the transducer element 12 together with the backing 13 and the positive lens 14 are arranged cardanically pivotable in a housing 15. The latter is filled with a fluid acoustic propagation medium, for example water, and has an application end provided with a coupling membrane 16 with which the ultrasound applicator 11 can be pressed against the body surface of the patient P for acoustic coupling.

The ultrasound applicator 11 has an adjustment means 17 allocated to it that serves the purpose of aligning the transducer element 12 together with backing 13 and positive lens 14 such that the focus F lies within the therapeutic ultrasound waves emanating from the transducer element 12, especially within the focus zone FZ' thereof. The focus zone FZ' has the approximate shape of an ellipsoid and is indicated with broken lines.

A drive unit 18 is allocated to the ultrasound applicator 11 and supplies it with the current required for generating therapeutic ultrasound waves.

The adjustment unit 6 and the drive unit 10 as well as the adjustment unit 17 and the drive unit 18 are in communication with a control unit 19 to which a keyboard that serves the purpose of operating the therapy apparatus is connected. The adjustment unit 6 and the adjustment unit 17 contain position sensors, for example inductive position sensors that supply signals corresponding to the position of the therapeutic ultrasound transducers 2 as well as supplying signals corresponding to the spatial alignment of the transducer element 12 relative to the ultrasound source 1 to the control unit 19 via lines 21 and 22. Proceeding on the basis of these signals, the control unit 19 calculates, first, the position of the center of that region in which the focus zones FZ of the therapeutic ultrasound transducers 2 superimpose and, second, the position of that point in which the acoustic axis A' of the ultrasound applicator 11 intersects plane E that can be scanned with the therapeutic ultrasound transducer 3. The control unit 19 forwards corresponding signals via the line 23 to the control and image-generating electronics 4, which mixes corresponding marks M1 (superimposition of the focus zones FZ) and M2 (intersection of A' with E) into the ultrasound image, as indicated in FIG. 2.

For the implementation of the treatment, the adjustment unit 6 and the adjustment unit 17 are actuated such via the keyboard 20 that the marks M1 and M2 are located within the image F' of the focus F in the ultrasound image. When this is the case, the treatment can be started, with different operating modes selectable with the keyboard 20 being possible.

It is essential for the different operating modes that the therapeutic ultrasound waves emanating from the ultrasound applicator 11 are relatively weakly focussed. When the ultrasound applicator 11 emits, for example, ultrasound with a frequency of 875 kHz and having a diameter of 3 cm, then a "natural" focus zone FZ' having a diameter of about 10 mm arises at the distance of about 10 cm without further measures for focussing. By comparison thereto, the therapeutic ultrasound waves emitted by the ultrasound transducers 2 of the ultrasound source 1 are comparatively highly focussed. For example, a focal length of 4 cm and a diameter of the "natural" focus zone FZ of 1.8 mm and a length of the focus zone of 20 mm arise for a diameter of the ultrasound transducers 2 of 2 cm and a frequency of the ultrasound waves emitted by the ultrasound transducers 2 of 2 MHz. The center of that region wherein the two focus zones FZ are superimposed can be brought as close as three centimeters to the ultrasound transducers 2, or can be moved as far as a distance of five centimeters away from them. It is self-evident that a sharper focussing can be achieved due to the acoustic positive lenses 14 or 9. It is also clear that other values are possible given employment of ultrasound transducers 2 having variable focal length. The different size of the focus zones FZ and FZ' is critical in any case. The aforementioned dimensions of the focus zones FZ and FZ' refer, moreover, to the −6 dB isobars, i.e. the focus zone is that region wherein the maximum acoustic pressure of the ultrasound waves is at least equal to half the acoustic pressure in the focus zone.

In the first of the operating modes, the control unit 19 sets the intensity of the ultrasound waves generated by the ultrasound transducers 2 by appropriately influencing the drive unit 10 such that the intensity resulting in the region of the overlap of the focus zones FZ is not yet adequate in order to effect the desired therapeutic effect, for example a necrotization. The intensity of the ultrasound waves emanating from the ultrasound applicator 11 is set by the control unit 19 by appropriate drive of the drive unit 18 such that an intensity adequate for achieving the desired therapeutic effect is present within the focus zone of the therapeutic ultrasound waves emanating from the ultrasound applicator 11 given superimposition with the therapeutic ultrasound waves emanating from the ultrasound transducers 2. This region, which is the region W of therapeutic influence of the therapy means, can then be displaced within the focus zone FZ' of the ultrasound applicator 11 by gradually modifying the alignment of the ultrasound transducers 2 relative to one another such that the region W of influence covers the entire part of the focus F lying within the ends E in a scan motion. This operation can be tracked on the basis of the marks M1 and M2 mixed into the ultrasound image. The emission of the therapeutic ultrasound waves thereby expediently ensues not continuously but pulse-like with respect to at least the ultrasound applicator 11 or at least one of the ultrasound transducers 3, so that a therapeutic effect can occur only when the pulse-like emission also ensues in addition to a (possibly) continuous emission of therapeutic ultrasound waves. The modification of the alignment of the therapeutic ultrasound transducers 2 relative to one another thereby ensues manually or with the control unit 19 between successive pulse-like emissions.

When the region W of influence is displaced with the control unit 19, a region to be treated can be marked in the ultrasound image with a light pen 24, whereupon the control unit 19 displaces the region W of influence within the marking by corresponding actuation of the adjustment unit 6 and, possibly, of the adjustment means 17.

A further operating mode is provided for treatment cases wherein the focus F is located in close proximity to the esophagus Ö. In such instances, the ultrasound intensity that can be produced with the ultrasound transducers 2 of the ultrasound source 1 suffices (under certain circumstances) for achieving the desired therapeutic effect, so that the activation of the ultrasound applicator 11 is omitted in this operating mode.

In instances wherein the region to be treated is located at a greater distance from the esophagus Ö, a third operating mode is selected wherein the therapeutic ultrasound transducer 3 is again used in addition to the ultrasound transducers 2 of the ultrasound source 1 and in addition to the ultrasound applicator 11 to emit therapeutic ultrasound waves, namely during the intervals that lie between the production of the ultrasound images. It is still possible in this mode to produce an ultrasound intensity adequate for achieving a therapeutic effect in regions situated relatively far from the esophagus Ö. The corresponding drive unit for the therapeutic ultrasound transducer 3 connected to the control unit 19 is not shown in FIG. 1.

As a consequence of the mechanical motion of the heart H due to heart activity, the treatment of the focus F with therapeutic ultrasound waves cannot ensue at arbitrary points in time. On the contrary, a triggering of the therapeutic ultrasound waves or of the pulse-like emission that is synchronized with the heart activity is required. To this end, a schematically indicated cardiography apparatus 28 with an electrode 29 is provided that emits an electrical signal corresponding to the heart activity to the control unit 29 that triggers a pulse-like treatment with therapeutic ultrasound when the heart is at relative mechanical rest. This preferably occurs in the diastole, namely in the time span between the end of the T-wave and the beginning of the QRS complex. This time span lasts about 0.5 sec. given a heart rate of 75 beats per minute.

The control unit 19 sets the intensities of the therapeutic ultrasound waves emanating from the ultrasound transducers 2 and, as warranted, from the ultrasound applicator 11 as well as, if necessary, from the diagnostic ultrasound transducer 3 such that an energy density of the therapeutic ultrasound waves arises in the region W of influence that is sufficient to produce the desired therapeutic effect in the tissue located in the region W of influence during one heart cycle.

Given the occurrence of pathological phenomena, moreover, there is the possibility of determining the spatial position of the respective pathogenic focus F by EKG mapping or with the assistance of a magnetocardiography apparatus. Corresponding data can be entered with the keyboard 20 before the treatment. On the basis of these data, the control unit calculates that position of the ultrasound source 1 in which the focus F is located within the plane that can be scanned with the diagnostic ultrasound transducer 3 and actuates the adjustment unit 6 so that it moves the ultrasound source 1 within the esophagus Ö into the corresponding position and correspondingly aligns the therapeutic ultrasound transducers 2. Moreover, the control unit 19 forwards a signal to the control and image-generating electronics 4, this signal serving the purpose of mixing a mark F" that characterizes the input position of the focus F into the ultrasound image. This is advantageous especially when the focus F cannot be recognized in the ultrasound image without further measures.

The control and image-generating electronics 4 has an evaluation electronics 35 allocated to it that serves the purpose of comparing ultrasound images produced at the same points in time of successive heart actions in order to detect temperature increases by this comparison in a known way. By comparing the identified temperature increase to a threshold that corresponds to the temperature required for the desired therapeutic effect, those regions can be detected wherein a temperature increase adequate for the desired therapeutic effect was achieved between two successive ultrasound images. The evaluation electronics 35 forwards the corresponding data to the control and image-generating electronics 4 that marks the corresponding location in the current ultrasound image, for example with a distinctive coloring. A good monitoring of the therapy procedure is possible in this way, so that misdirections of the ultrasound locating means caused by refraction and diffraction phenomena in the tissue of the patient and deviations between the actual and the theoretical position of the region of influence of the therapeutic ultrasound waves do not influence the treatment.

The structure of the esophageally applied ultrasound source 1 shall be set forth in greater detail below. According to FIGS. 1 through 6, the ultrasound source 1 has a flexible, hose-like sheath 40. This is closed at its distal end and contains the acoustic propagation medium for the ultrasound waves emanating from the therapeutic ultrasound transducers 2 and from the diagnostic ultrasound transducer 3.

A chain structure generally referenced 41 is located inside the sheath 40, the elements 42 thereof having a C-shaped cross-section at least in the region of the therapeutic ultrasound transducer 2 and the diagnostic ultrasound transducer 3. The elements 42 can having an oval cross-section in the remaining regions of the chain structure 41. The elements 42 are provided with bores lying opposite one another and proceeding parallel to their longitudinal axes, these bores serving for the acceptance of the traction elements 43 of two Bowden cables. The traction elements 43 are provided with clamp members 56 with which they lie against that end face of the corresponding element 42 neighboring the distal end of the sheath 40. The envelopes 44 of the Bowden cables are supported against that end face of the element 42 arranged closest to the proximal end of the sheath 40 that faces toward the proximal end of the sheath 40.

Figure 3:
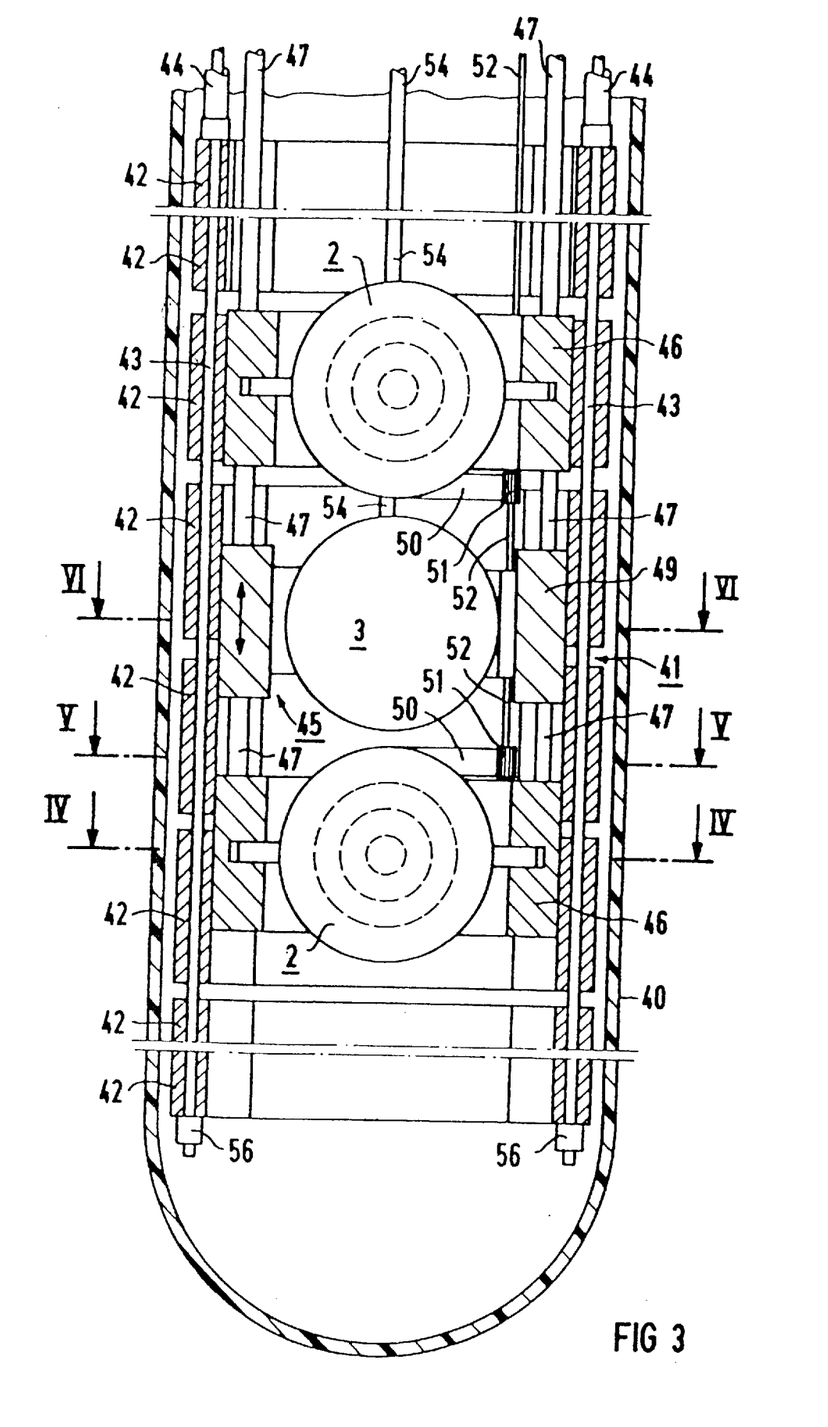
FIG. 3 illustrates the transesophageally applied ultrasound source of the apparatus of FIGS. 1 and 2 in a longitudinal section.

Tensioning means that are not shown are allocated to the Bowden cables. When these are in their loosened condition, a space is present between each pair of neighboring elements 42, as shown in FIG. 3, so that the chain structure 41 is flexible. The ultrasound source 1 can then be easily introduced into the esophagus of the patient P to be treated. When the tensioning means are actuated, the elements 42 lie against one another with their plane-parallel end faces, so that the chain structure 41 assumes the straight-line shape indicated in FIG. 1.

A carriage structure 45 that carries the therapeutic ultrasound transducers 2 and the diagnostic ultrasound transducer 3 is situated inside the elements 42. In detail, two sliding blocks 46 that are connected to one another by two flexible wires 47 are provided. One of the therapeutic ultrasound transducers 2 is connected to each of the sliding blocks 46 as described below. A carrier part 49 to which the diagnostic ultrasound transducer 3 is secured is arranged centrally between the sliding blocks 46 that are guided in slideways 48 of the elements 42 in the way to be seen from FIG. 4. The carriage structure 45 is longitudinally displaceable within the chain structure 41 with the wires on which the adjustment unit 6 acts, this being indicated by a corresponding double arrow.

The backings 7 of the therapeutic ultrasound transducers 2 have pegs accepted into corresponding bores of the sliding blocks 46, so that the therapeutic ultrasound transducers 2 are pivotable in the way already set forth. A gearwheel segment 50 that interacts with two corresponding pinions 51 is attached to each of the therapeutic ultrasound transducers. The pinions 51 are torsionally attached to a flexible wire 52 rotatably seated in corresponding bores of the sliding blocks 46.

The gearwheel segments 50 and the pinions 51 are dimensioned, and the gearwheel segments 50 are attached, to the therapeutic ultrasound transducers 2 such that a synchronous swivel motion of the therapeutic ultrasound transducers 2 toward one another or away from one another ensues when the wire 52 is turned by the adjustment unit 6.

The diagnostic ultrasound transducer 3 is pivotably seated at the carrier part 49 with a drag bearing 53 such that the aforementioned body slice of the patient P can be scanned. The swivel motion is transmitted from the drive unit 25 onto the diagnostic ultrasound transducer 3 with a flexible wire 54.

Figure 5:
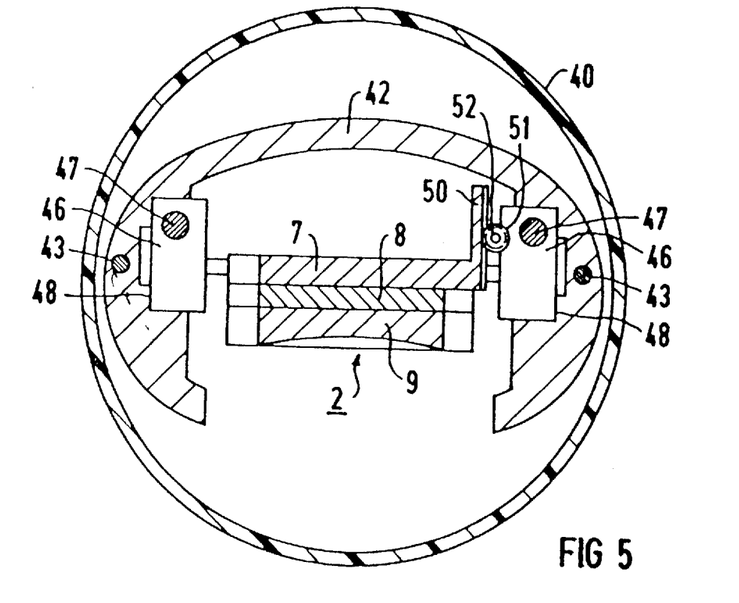
Figure 6:
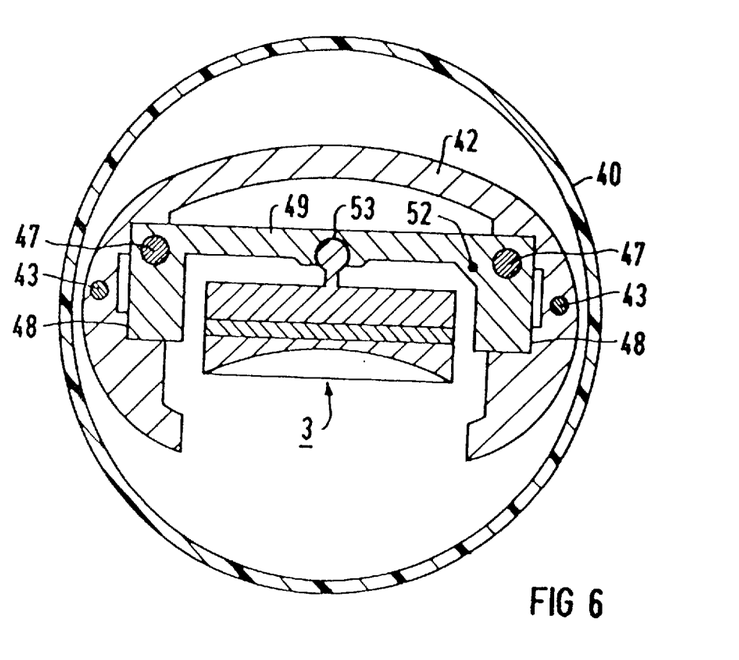

For clarity, the electrical lines leading to the ultrasound transducers 2 and 3 are not shown in FIGS. 4 through 6.

Broken-line circles in FIG. 4, moreover, indicate that the therapeutic ultrasound transducers 2 can be electronically focussed ring structures.

It can be expedient in some treatment cases to provide yet another extracorporeally applied ultrasound applicator 55 in addition to the ultrasound source 1 and the ultrasound applicator 11. This is indicated with broken lines in FIG. 1. The ultrasound applicator 55 is intercostally applied, i.e. it emits ultrasound between two neighboring ribs of the patient P. The therapeutic ultrasound waves emitted by the ultrasound applicator 55 are preferably weakly focussed. The drive and the alignment of the ultrasound applicator 55 ensue in a way not shown but which is analogous to the case of the ultrasound applicator 11.

In the described exemplary embodiment, an ultrasound source that is transesophageally applied as well as at least one ultrasound applicator that can be extracorporeally applied are present. It can be within the scope of the invention, however, for the therapy apparatus to have either only one transesophageally applied ultrasound source or, alternatively, only extracorporeally applied ultrasound applicators, or only one such ultrasound applicator.

In the exemplary embodiment set forth above, a pathogenic focus F in the region of the heart H itself is treated. It is self-evident that (blood) vessels, particularly heart-proximate vessels, can also be treated with an inventive therapy apparatus.

Although modifications and changes may be suggested by those skilled in the art, it is the intention of the inventor to embody within the patent warranted hereon all changes and modifications as reasonably and properly come within the scope of his contribution to the art.

I claim:

1. A therapy apparatus for treating cardiovascular conditions comprising:
    an ultrasound source having means for generating therapeutic ultrasound waves having a therapeutically effective region and having an intensity for producing tissue modifications by thermal interaction with tissue located in said therapeutically effective region, said ultrasound source having dimensions adapted for intrathoracically applying said ultrasound source in a subject, and said therapeutic ultrasound source containing a plurality of spatially separated therapeutic ultrasound transducers mechanically connected in a linear structure and means for spatially orienting said therapeutic ultrasound transducers relative to each other for causing therapeutic ultrasound waves emitted by each therapeutic ultrasound transducer to be superimposed at a location to be treated.

2. A therapy apparatus as claimed in claim 1 wherein said means for generating therapeutic ultrasound waves comprises means for generating therapeutic ultrasound waves having an intensity for necrotizing said tissue located in said therapeutically effective region.

3. A therapy apparatus as claimed in claim 1 wherein said means for generating therapeutic ultrasound waves comprises means for generating therapeutic ultrasound waves having an intensity for interacting with said tissue located in said therapeutically effective region for permanently modifying said tissue.

4. A therapy apparatus as claimed in claim 1 wherein said ultrasound source further comprises a diagnostic ultrasound transducer and wherein said apparatus further comprises ultrasound locating means, connected to said diagnostic ultrasound transducer, for locating said region to be treated.

5. A therapy apparatus as claimed in claim 4 wherein said therapeutic ultrasound transducers and said diagnostic ultrasound transducer are mechanically connected in a structure in said ultrasound source of which said therapeutic ultrasound transducers and said diagnostic ultrasound transducer comprise a plurality of successive elements, said structure having an arrested condition and a non-arrested condition, and further comprising means for placing said structure in said non-arrested condition for making said structure flexible and for placing said structure in said arrested condition for making said structure rigid.

6. A therapy apparatus as claimed in claim 5 wherein said structure comprises a chain.

7. A therapy apparatus as claimed in claim 1 wherein said therapeutic ultrasound transducers are mechanically connected in a structure in said ultrasound source of which said therapeutic ultrasound transducers comprise a plurality of successive elements, said structure having an arrested condition and a non-arrested condition, and further comprising means for placing said structure in said non-arrested condition for making said structure flexible and for placing said structure in said arrested condition for making said structure rigid.

8. A therapy apparatus as claimed in claim 7 wherein said structure comprises a chain.

9. A therapy apparatus as claimed in claim 1 further comprising means for enabling emission of said therapeutic ultrasound waves from said therapeutic ultrasound transducers only during pauses in cardiac activity of said subject wherein the heart of said subject is at relative mechanical rest.

10. A therapy apparatus as claimed in claim 1 further comprising an extracorporeally applicable therapeutic ultrasound source.

11. A therapy apparatus as claimed in claim 10 wherein said extracorporeally applicable therapeutic ultrasound source comprises an intercostally applicable therapeutic ultrasound source.

12. A therapy apparatus as claimed in claim 10 wherein said extracorporeally applicable therapeutic ultrasound source comprises a subcostally applicable therapeutic ultrasound source.

13. A therapy apparatus as claimed in claim 10 wherein said extracorporeally applicable therapeutic ultrasound source emits further therapeutic ultrasound waves, and said therapy apparatus further comprising means for aligning said extracorporeally applicable therapeutic ultrasound source and said ultrasound source for superimposing said further therapeutic ultrasound waves and said therapeutic ultrasound waves at least in said therapeutically effective region.

14. A therapy apparatus as claimed in claim 13 wherein said extracorporeally applicable therapeutic ultrasound source comprises means for focusing said further therapeutic ultrasound waves onto a first focus zone.

15. A therapy apparatus as claimed in claim 14 wherein said ultrasound source comprises means for focusing therapeutic ultrasound waves emitted from at least one of said therapeutic ultrasound transducers onto a second focus zone.

16. A therapy apparatus as claimed in claim 15 wherein said first and second focus zones have respectively different sizes, with one of said focus zones being larger than the other, and further comprising means for displacing a smaller of said focus zones within a larger of said focus zones.

17. A therapy apparatus as claimed in claim 13 wherein said extracorporeally applicable therapeutic ultrasound source comprises means for emitting said further therapeutic ultrasound waves in pulses.

18. A therapy apparatus as claimed in claim 17 wherein said ultrasound source comprises means for operating at least one of said therapeutic ultrasound transducers for emitting said therapeutic ultrasound waves in pulses.

19. A therapy apparatus as claimed in claim 18 wherein said ultrasound source and said extracorporeally applicable therapeutic ultrasound source comprise, in combination, means for superimposing said therapeutic ultrasound waves and said further therapeutic ultrasound waves in said therapeutically effective region with an energy density and a pulse duration for producing a therapeutic effect in a heart of said subject during one heart cycle.

20. A therapy apparatus as claimed in claim 1 wherein said ultrasound source comprises means for operating at least one of said therapeutic ultrasound transducers for emitting said therapeutic ultrasound waves in pulses.

21. A therapy apparatus as claimed in claim 20 wherein said ultrasound source comprises means for operating said therapeutic ultrasound transducers for emitting said therapeutic ultrasound waves with an energy density and a pulse duration in said therapeutically effective region for producing a therapeutic effect in a heart of said subject during one heart cycle.

22. A therapy apparatus as claimed in claim 1 further comprising means for determining a temperature of tissue in said therapeutically effective region.

23. A therapy apparatus as claimed in claim 22 wherein said means for determining a temperature comprises means for obtaining a succession of ultrasound images, and means for identifying said temperature from said successive ultrasound images.

24. A therapy apparatus as claimed in claim 1 wherein said ultrasound source having dimensions adapted for intrathoracically applying ultrasound source in a subject comprises a transesophageally applicable ultrasound source.

25. A method for treating cardiovascular conditions in a subject comprising the steps of:
   intrathoracially insonifying a cardiovascular region to be treated with therapeutic ultrasound waves having a therapeutically effective region; and
   generating said therapeutic ultrasound waves with an intensity for producing cardiovascular tissue modifications due to thermal effect in cardiovascular tissue disposed in said therapeutically effective region.

26. A method as claimed in claim 25 wherein the step of generating said therapeutic ultrasound waves with an intensity comprises generating said therapeutic ultrasound waves with an intensity for necrotizing said cardiovascular tissue in said therapeutically effective region.

27. A method as claimed in claim 25 comprising the additional step of introducing a source of said therapeutic ultrasound waves into the esophagus of said subject, and wherein the step of intrathoracially insonifying said cardiovascular region with therapeutic ultrasound waves comprises insonifying said cardiovascular region with therapeutic ultrasound waves emitted from said therapeutic ultrasound source in said esophagus.

28. A method as claimed in claim 25 comprising the additional step of:
   insonifying said cardiovascular tissue with further therapeutic ultrasound waves; and
   generating said further therapeutic ultrasound waves from an extracorporeally applied therapeutic ultrasound source.

29. A method as claimed in claim 28 wherein the step of generating said further therapeutic ultrasound waves comprises generating said further therapeutic ultrasound waves from an intercostally applied therapeutic ultrasound source.

30. A method as claimed in claim 28 wherein the step of generating said further therapeutic ultrasound waves comprises generating said further therapeutic ultrasound waves from a subcostally applied therapeutic ultrasound source.

31. A method as claimed in claim 28 wherein the step of intrathoracically insonifying a cardiovascular region comprises intrathoracically insonifying said cardiac region with an intrathoracic source of said therapeutic ultrasound waves, and comprising the additional step of aligning said intrathoracic source of said therapeutic ultrasound waves and said extracorporeally applied therapeutic ultrasound source for superimposing said therapeutic ultrasound waves and said further therapeutic ultrasound waves in said therapeutically effective region.

* * * * *